(12) United States Patent
Gururajan et al.

(10) Patent No.: US 10,799,506 B2
(45) Date of Patent: Oct. 13, 2020

(54) RIBOCICLIB TABLET (71) Applicant: Novartis AG, Basel (CH)

(72) Inventors: Bindhumadhavan Gururajan, Basel (CH); Arnaud Grandeury, Basel (CH); Rui Costa, Basel (CH)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 15/564,534

(22) PCT Filed: Apr. 14, 2016

(86) PCT No.: PCT/IB2016/052136
§ 371 (c)(1),
(2) Date: Oct. 5, 2017

(87) PCT Pub. No.: WO2016/166703
PCT Pub. Date: Oct. 20, 2016

(65) Prior Publication Data
US 2018/0071292 A1    Mar. 15, 2018

Related U.S. Application Data (60) Provisional application No. 62/148,240, filed on Apr. 16, 2015.

(51) Int. Cl.
| | |
|---|---|
| *A61K 31/519* | (2006.01) |
| *A61K 9/20* | (2006.01) |
| *A61K 31/496* | (2006.01) |
| *A61K 9/28* | (2006.01) |

(52) U.S. Cl.
CPC .......... *A61K 31/519* (2013.01); *A61K 9/2027* (2013.01); *A61K 9/2054* (2013.01); *A61K 9/2077* (2013.01); *A61K 9/284* (2013.01); *A61K 31/496* (2013.01)

(58) Field of Classification Search
CPC .... A61K 9/2027; A61K 9/2054; A61K 9/284; A61K 9/2077; A61K 31/519; A61K 31/496
See application file for complete search history.

(56) References Cited

FOREIGN PATENT DOCUMENTS

| | | |
|---|---|---|
| EP | 2 742 940 A1 * | 6/2014 |
| EP | 2742940 | 6/2014 |
| WO | 2012064805 | 5/2012 |
| WO | 2014097125 | 6/2014 |
| WO | WO 2014097125 A1 * | 6/2014 |

OTHER PUBLICATIONS

Zhang Y-X et al., Antiproliferative Effects of CDK4-Amplified Human Liposarcoma in Vitro and In Vito. Mol Cancer Ther., vol. 13, Nol 9, pp. 2184-2193, 2014.

* cited by examiner

*Primary Examiner* — Blessing M Fubara
(74) *Attorney, Agent, or Firm* — David K. Cheng (57) ABSTRACT

The present disclosure is directed to oral tablet of ribociclib including its salt(s). One embodiment of the present disclosure is directed to tablet of ribociclib with high drug load with an immediate release profile. One embodiment of the present disclosure is directed to coated tablet of ribociclib. Another embodiment of the present disclosure is directed to coated tablet of ribociclib where the coating is an advanced moisture barrier coating (e.g., Opadry® amb II coating where the coating is PVA based).

14 Claims, 5 Drawing Sheets

DVS data on the Ribociclib Tablets with standard Opadry® (aka Opadry 1, HMPC coating) and Opadry® amb II (aka Opadry 2, AMB functional coating)

FIG. 1A Process flow diagram

FIG. 1B  Process flow diagram (Continued)

Fig. 2:

(A) Tablet with Opadry® (Standard HPMC);
(B) Tablet with Opadry® amb II (with AMB coating, PVA based)

FIG. 3  DVS data on the Ribociclib Tablets with standard Opadry® (aka Opadry 1, HMPC coating) and Opadry® amb II (aka Opadry 2, AMB functional coating)

FIG. 4 Dissolution profile of Ribociclib (LEE011) tablets coated with Opadry® amb II

RIBOCICLIB TABLET

FIELD OF THE INVENTION

The present disclosure relates to tablet formulation of ribociclib and/or its pharmaceutically acceptable salts, as well as methods of treatment using the same.

BACKGROUND ART

The compound of Formula (I)

(I)

is known as ribociclib. Its chemical name is 7-cyclopentyl-N,N-dimethyl-2-{[5-(piperazin-1-yl)pyridin-2-yl]amino}-7H-pyrrolo[2,3-d]pyrimidine-6-carboxamide and its synthesis is specifically described in WO 2010/020675 A1, Example 74.

The succinate salt of ribociclib is described by Formula (II):

(II)

and is described in WO2012/064805.

Ribociclib and its pharmaceutically acceptable salt(s) have valuable pharmacological properties and can be used, for example, (1) as inhibitors of cyclin dependent kinases, (in particular, cyclin dependent kinases selected from CDK1, CDK2, CDK3, CDK4, CDK5, CDK6 and CDK9); and (2) as modulators and/or inhibitors of glycogen synthase kinase-3 (GSK-3).

Ribociclib is also known under the code name LEE011.

SUMMARY OF THE INVENTION

The present disclosure is directed to oral formulations of ribociclib including its salt(s) and/or solvate(s). One embodiment of the present disclosure is directed to tablet formulations of ribociclib with high drug load with an immediate release profile. One embodiment of the present disclosure is directed to coated tablet formulations of ribociclib. Another embodiment of the present disclosure is directed to coated tablet formulations of ribociclib where the coating is an advanced moisture barrier coating (e.g., Opadry® amb II coating where the coating is PVA based).

BRIEF DESCRIPTION OF THE DRAWINGS

The invention is illustrated by reference to the accompanying drawing described below.

DETAILED DESCRIPTION OF THE INVENTION

The present disclosure relates to a solid oral tablet dosage form of ribociclib or its pharmaceutically acceptable salt. Such formulation has very good process performance and high stability.

The tablet of the present disclosure has an immediate release profile. These tablets release at least 75% (Q) (where Q refers to the acceptance criteria defined by USP chapter <711>) of the active after 45 minutes under standard dissolution test. In embodiment, the tablets release at least 75% of the active after 45 minutes when using the rotating basket at 100 rpm, with 900 ml of HCl pH 1 as dissolution medium at 37° C. In another embodiment, the tablets release at least 75% of the active after 45 minutes when using the rotating basket at 100 rpm, with 900 ml of HCl pH 2 as dissolution medium at 37° C. In another embodiment, the tablets release at least 75% of the active after 45 minutes when using the rotating basket at 100 rpm, with 900 ml of acetate buffer pH 4.5 as dissolution medium at 37° C. In another embodiment, the tablets release at least 75% of the active after 45 minutes when using the rotating basket at 100 rpm, with 900 ml of phosphate buffer pH 6.8 as dissolution medium at 37° C.

The tablets of the present disclosure can be coated or uncoated.

The tablets of the present disclosure have high drug load of at least 40%, 45%, 50%, 55% or 60%, when measured in w/w percentage of the ribociclib succinate of the core tablet.

The tablets of the present disclosure have high drug load of at least 32%, 40%, 44%, 47% or 52%, when measured in w/w percentage of the ribociclib free base of the core tablet.

The % of ribociclib succinate (w/w) is at least 40% of the core tablet. In one embodiment, the % of ribociclib succinate (w/w) is at least 50% of the core tablet. In another embodiment, the % of ribociclib succinate (w/w) is at least 55% of the core tablet. In another embodiment, the % of ribociclib succinate (w/w) is at about 55% to 65% of the core tablet. In another embodiment, the % of ribociclib succinate (w/w) is at about 60% of the core tablet.

When measured in terms of ribociclib free base, the % of ribociclib (w/w) is at least 32% of the core tablet. In one embodiment, the % of ribociclib (w/w) is at least 40% of the core tablet. In another embodiment, the % of ribociclib (w/w) is at least 44% of the core tablet. In another embodiment, the % of ribociclib (w/w) is at about 44% to 52% of the core tablet. In another embodiment, the % of ribociclib (w/w) is at about 47% of the core tablet.

Core tablet is also referred to as "tablet core".

In an uncoated tablet, the tablet core is the whole tablet. In a coated tablet, the tablet core is the portion of the tablet excluding the coating.

The tablet formulation according to the disclosure may contain pharmaceutically acceptable excipients commonly used in pharmaceutical formulations, particularly those for oral administration for example, as fillers, binders, disintegrants and lubricants.

Fillers, for example, can be cellulose, mannitol, di-calcium phosphate, lactose, microcrytalline cellulose, alone or in combination thereof.

Binders, for example, can be hydroxypropyl cellulose, polyvinyl-pyrrolidone, alone or in combination thereof.

Disintegrants, for example, can be crosslinked polyvinyl-pyrrolidone, crosslinked sodium carboxymethyl cellulose, low substituted hydroxypropyl cellulose, sodium starch gly-colate, alone or in combination thereof.

Lubricants, for example, can be magnesium stearate, stearic acid, talc, silicon dioxide, sodium stearyl fumarate, alone or in combination thereof.

Figure 1A:
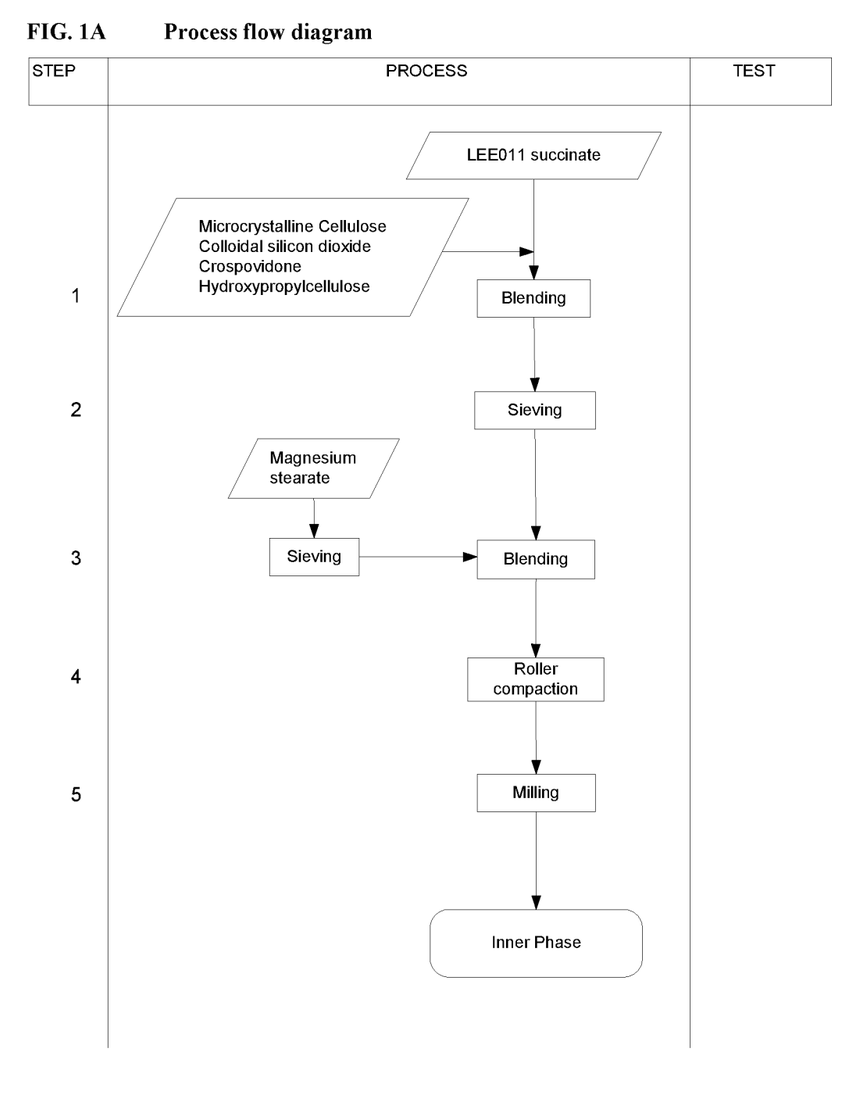
FIGS. 1A and 1B depict a process flow diagram for making ribociclib tablets. Uncoated tablets are made according to Steps 1-8. Coated tablets are made according to Steps 1-9.
Figure 1B:
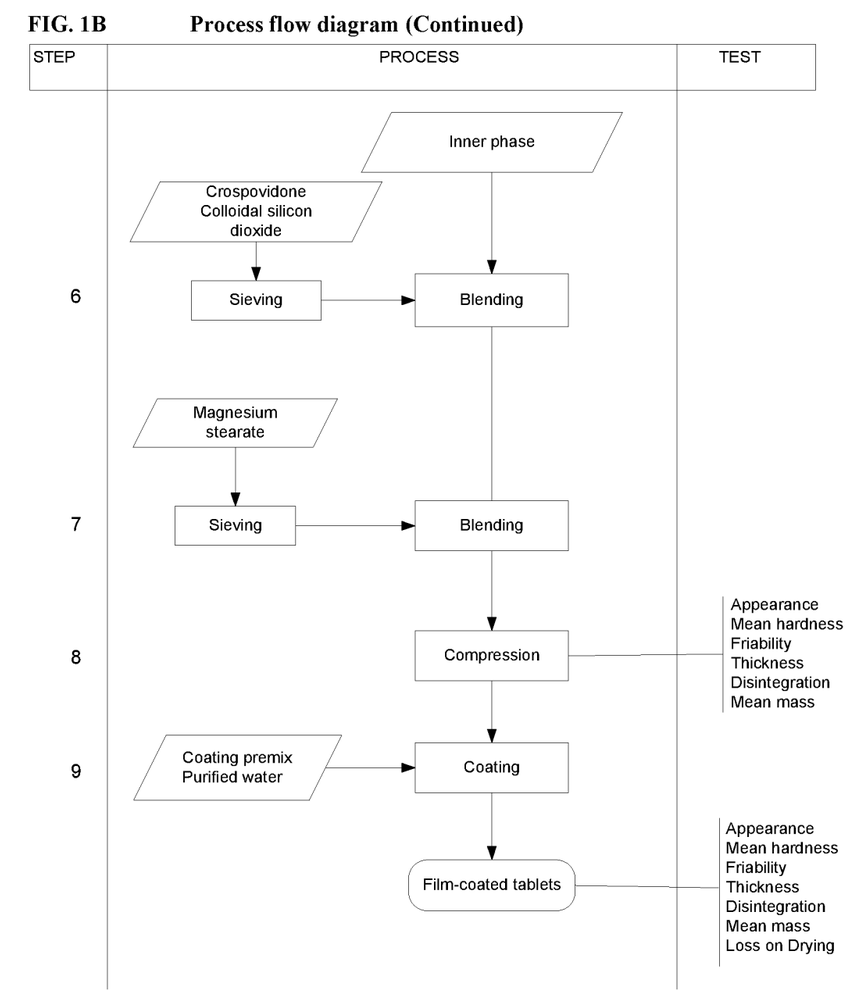

As an example, FIGS. 1A and 1B show the process flow diagram of making ribociclib tablets. Uncoated tablets are made according to Steps 1-8. Coated tablets are made according to Steps 1-9.

In one embodiment, the core ribociclib tablets have an inner phase comprising ribociclib or salt(s) thereof, and an outer phase.

Coating Material:

The ribociclib tablets of the present disclosure are immediate release tablets and can be coated with any immediate release coating materials. For example, the coating material can be Opadry®, Opadry® 200, Opadry® amb II, Opadry® Fx™, Opadry® II, Opalux®, or mixtures thereof. Opadry®, Opadry® 200, Opadry® amb II, Opadry® Fx™, Opadry® II, and Opalux® are all commercially available through Colorcon, Inc.

In one embodiment, the coating material is Opadry®. Opadry® is a HPMC (hydroxypropyl methylcellulose) coating material and has the following composition: HPMC (Pharmacoat 603) 71.4%, polyethylene glycol 7.15%, talc 7.15%, and iron oxide 14.3%.

In another embodiment, the coating material is Opadry® amb II. Opadry® amb II is a PVA (polyvinyl alcohol) based coating material and has the following composition: polyvinyl alcohol 45.52%, iron oxide 32%, talc 20%, lecithin (soya) 2%, and xanthan gum 0.48%.

When the ribociclib tablets are coated with Opadry® amb II, the tablets show improved appearances and are essentially free of cracking defects.

The present invention(s) is further described in the following example. The following non-limiting examples illustrate the invention(s) and are not to be construed as limiting the scope of the appended claims.

Example 1

Uncoated 50 mg and 200 mg Ribociclib Tablets

Table 1 below details the composition of uncoated 50 mg and 200 mg ribociclib tablets. These tablets are made according to Steps 1-8 of the process flow diagram (FIGS. 1A-1B).

TABLE 1

Composition per dosage form unit

| Ingredient | Composition per unit [mg/unit] | |
|---|---|---|
| | 50 mg of Ribociclib | 200 mg of Ribociclib |
| Inner phase | | |
| Ribociclib (LEE011) succinate[1] | 63.600 | 254.40 |
| Microcrystalline cellulose/Cellulose, microcrystalline | 16.860 | 67.44 |
| Hydroxypropylcellulose | 12.030 | 48.12 |
| Crospovidone | 7.300 | 29.20 |
| Colloidal silicon dioxide/Silica, colloidal anhydrous | 0.530 | 2.12 |
| Magnesium stearate[2] | 1.590 | 6.36 |
| Outer phase | | |
| Crospovidone | 3.210 | 12.84 |
| Colloidal silicon dioxide/Silica, colloidal anhydrous | 0.265 | 1.06 |
| Magnesium stearate[2] | 2.115 | 8.46 |
| Tablet weight | 107.500 | 430.00 |

[1] The salt factor is 1.272. The drug substance quantity is increased if the content is ≤99.5% with a corresponding reduction in the microcrystalline cellulose content.
[2] Vegetable origin Example 2

Uncoated 100 mg, 150 mg and 300 mg Ribociclib Tablets

Table 2 below details the composition of uncoated 100 mg, 150 mg, and 300 mg ribociclib tablets. These tablets are made according to Steps 1-8 of the process flow diagram (FIGS. 1A-1B).

TABLE 2

Composition per dosage form unit

| Ingredient | Composition per unit [mg/unit] | | |
|---|---|---|---|
| | 100 mg of Ribociclib | 150 mg of Ribociclib | 300 mg of Ribociclib |
| Inner phase | | | |
| Ribociclib (LEE011) succinate[1] | 127.2 | 190.8 | 381.6 |
| Microcrystalline cellulose/Cellulose, microcrystalline | 33.72 | 50.58 | 101.16 |
| Hydroxypropylcellulose | 24.06 | 36.09 | 72.18 |
| Crospovidone | 14.60 | 21.9 | 43.8 |
| Colloidal silicon dioxide/Silica, colloidal anhydrous | 1.06 | 1.59 | 3.18 |
| Magnesium stearate[2] | 3.18 | 4.77 | 9.54 |

TABLE 2-continued

Composition per dosage form unit

| Ingredient | Composition per unit [mg/unit] | | |
|---|---|---|---|
| | 100 mg of Ribociclib | 150 mg of Ribociclib | 300 mg of Ribociclib |
| Outer phase | | | |
| Crospovidone | 6.420 | 9.63 | 19.26 |
| Colloidal silicon dioxide/Silica, colloidal anhydrous | 0.53 | 0.795 | 1.59 |
| Magnesium stearate[2] | 4.23 | 6.345 | 12.69 |
| Tablet weight | 215.00 | 322.5 | 645.00 |

[1]The salt factor is 1.272. The drug substance quantity is increased if the content is ≤99.5% with a corresponding reduction in the microcrystalline cellulose content.
[2]Vegetable origin Example 3

Coated (with Opadry® Amb II Coating) 50 mg and 200 mg Ribociclib Tablets

Table 3 below details the composition of film-coated 50 mg and 200 mg ribociclib tablets. These tablets were made according to Steps 1-9 of the process flow diagram (FIGS. 1A-1B). The coating material is Opadry® amb II, which is commercially available and is an advanced moisture barrier (AMB) coating, PVA based.

TABLE 3

Composition per dosage form unit

| Ingredient | Composition per unit [mg/unit] | |
|---|---|---|
| | 50 mg of Ribociclib | 200 mg of Ribociclib |
| Inner phase | | |
| Ribociclib (LEE011) succinate[1] | 63.600 | 254.40 |
| Microcrystalline cellulose/ Cellulose, microcrystalline | 16.860 | 67.44 |
| Hydroxypropylcellulose | 12.030 | 48.12 |
| Crospovidone | 7.300 | 29.20 |
| Colloidal silicon dioxide/Silica, colloidal anhydrous | 0.530 | 2.12 |
| Magnesium stearate[2] | 1.590 | 6.36 |
| Outer phase | | |
| Crospovidone | 3.210 | 12.84 |
| Colloidal silicon dioxide/Silica, colloidal anhydrous | 0.265 | 1.06 |
| Magnesium stearate[2] | 2.115 | 8.46 |
| Core tablet weight | 107.500 | 430.00 |
| Coating[3] | | |
| Coating premix, white[4] | 0.774 | 3.096 |
| Coating premix, yellow[4] | 2.537 | 10.148 |
| Coating premix, red[4] | 0.774 | 3.096 |
| Coating premix, black[4] | 0.215 | 0.860 |
| Purified water[5] | Qs | Qs |
| Film coated tablet weight | 111.800 | 447.20 |

[1]The salt factor is 1.272. The drug substance quantity is increased if the content is ≤99.5% with a corresponding reduction in the microcrystalline cellulose content.
[2]Vegetable origin
[3]Excess coating is prepared to compensate for losses during the coating process
[4]The coating premix is a commercially available product
[5]Removed during processing Example 4

Coated (with Opadry® Amb II Coating) 100 mg, 150 mg and 300 mg Ribociclib Tablets Table 4 below details the composition of film-coated 100 mg, 150 mg and 300 mg ribociclib tablets. These tablets are made according to Steps 1-9 of the process flow diagram (FIGS. 1A-1B). The coating material is Opadry® amb II, which is commercially available and is an advanced moisture barrier (AMB) coating, PVA based.

TABLE 4

Composition per dosage form unit

| Ingredient | Composition per unit [mg/unit] | | |
|---|---|---|---|
| | 100 mg of Ribociclib | 150 mg of Ribociclib | 300 mg of Ribociclib |
| Inner phase | | | |
| Ribociclib (LEE011) succinate[1] | 127.2 | 190.8 | 381.6 |
| Microcrystalline cellulose/ Cellulose, microcrystalline | 33.72 | 50.58 | 101.16 |
| Hydroxypropylcellulose | 24.06 | 36.09 | 72.18 |
| Crospovidone | 14.60 | 21.9 | 43.8 |
| Colloidal silicon dioxide/Silica, colloidal anhydrous | 1.06 | 1.59 | 3.18 |
| Magnesium stearate[2] | 3.18 | 4.77 | 9.54 |
| Outer phase | | | |
| Crospovidone | 6.420 | 9.63 | 19.26 |
| Colloidal silicon dioxide/Silica, colloidal anhydrous | 0.53 | 0.795 | 1.59 |
| Magnesium stearate[2] | 4.23 | 6.345 | 12.69 |
| Core tablet weight | 215.00 | 322.5 | 645.00 |
| Coating[3] | | | |
| Coating premix, white[4] | 1.548 | 2.322 | 4.644 |
| Coating premix, yellow[4] | 5.074 | 7.611 | 15.222 |
| Coating premix, red[4] | 1.548 | 2.322 | 4.644 |
| Coating premix, black[4] | 0.43 | 0.645 | 1.29 |
| Purified water[5] | Qs | qs | qs |
| Film coated tablet weight | 223.6 | 335.4 | 670.8 |

[1]The salt factor is 1.272. The drug substance quantity is increased if the content is ≤99.5% with a corresponding reduction in the microcrystalline cellulose content.
[2]Vegetable origin
[3]Excess coating is prepared to compensate for losses during the coating process
[4]The coating premix is a commercially available product
[5]Removed during processing Example 5

Ribociclib tablets coated with different coatings (Opadry® (standard HPMC based) vs. Opadry® amb II (advance moisture barrier (AMB) coating material, PVA based)) were compared. Coating was carried out in Bohle coater 1 Kg scale with spray rate of 3 g/min. With standard Opadry® coating, tablet logo bridging issue and tablet cracking defects were observed. In contrast, no cracking was observed with the PVA based Opadry® amb II coated tablets.

Figure 2:
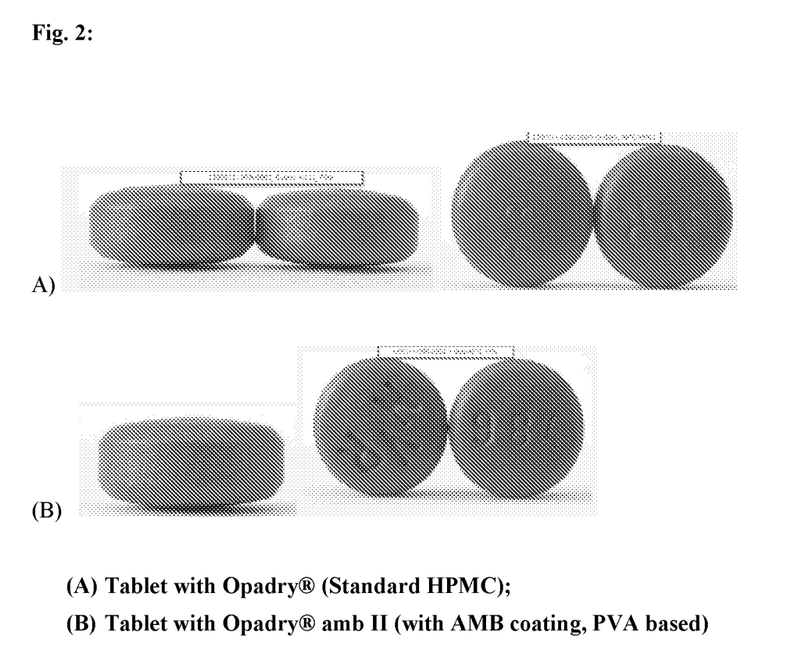
FIG. 2 shows the images of the tablets manufactured with Opadry® (standard HPMC based) and with Opadry® amb II (advance moisture barrier (AMB) coating material with PVA based).

FIG. 2 shows the images of the tablets manufactured with Opadry® (standard HPMC based) and with Opadry® amb II (advance moisture barrier (AMB) coating material with PVA based).

Example 6

Figure 3:
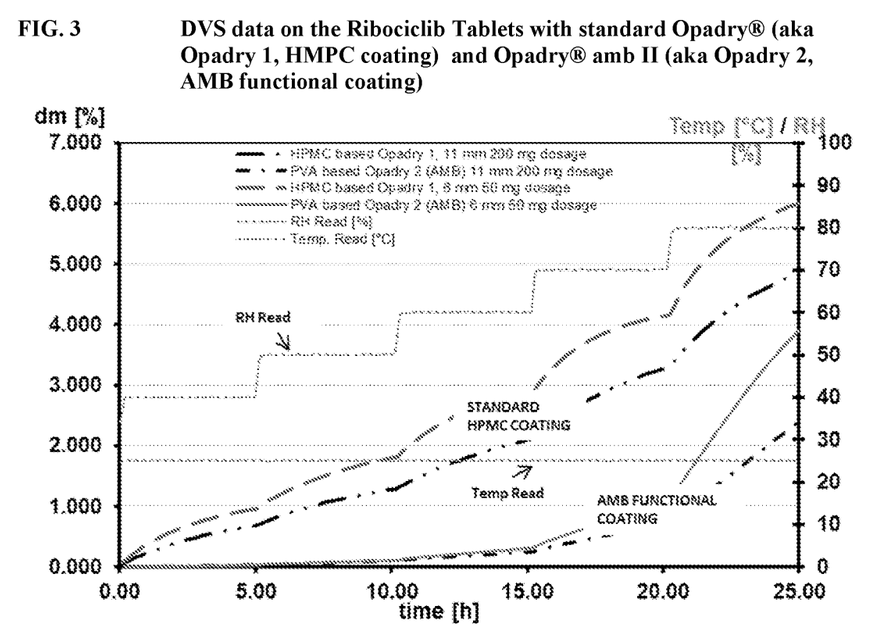
FIG. 3 shows the Dynamic Vapor Sorption (DVS) data of the ribociclib tablets coated with standard Opadry® and Opadry® amb II.

Dynamic vapor sorption (DVS) data on the ribociclib tablets coated with standard Opadry® and Opadry® amb II are presented in FIG. 3. At both 50 mg and 200 mg dosage unit, the tablets coated with the AMB coating (Opadry® amb II) show better performance than the standard Opadry® tablets.

Example 7

Figure 4:
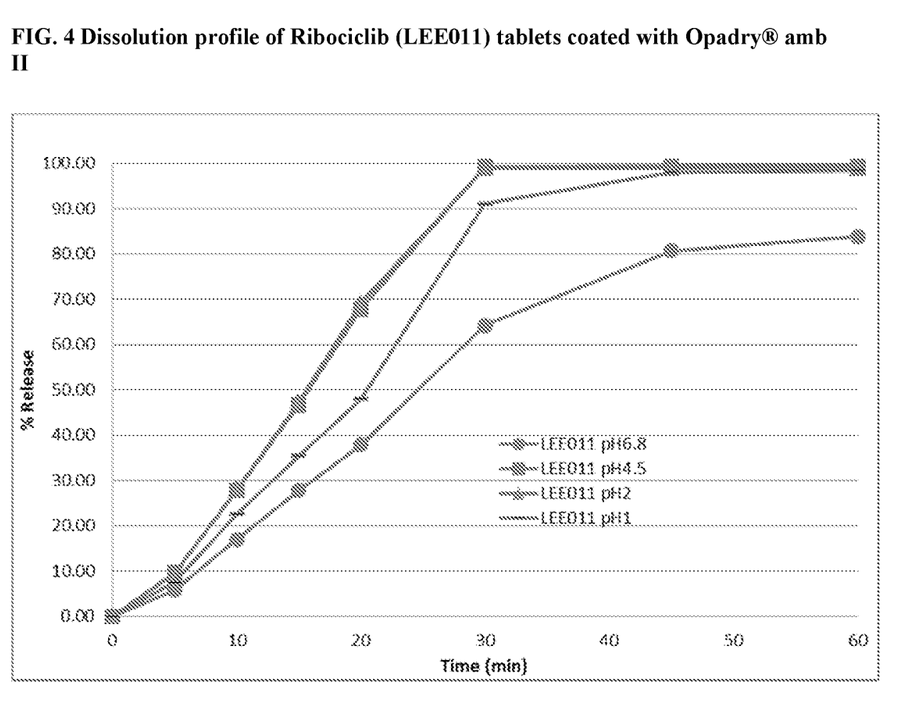
FIG. 4 shows the dissolution profile of ribociclib (LEE011) tablets coated with Opadry® amb II obtained with the rotating basket at 100 rpm with dissolution media having different pH values, at 37° C.

The dissolution profiles of the Opadry® amb II coated ribociclib tablets are evaluated in different pH media. Apparatus: basket, Rotation: 100 rpm, Volume: 900 mL, Media: HCl pH 1, HCl pH 2, acetate buffer pH 4.5, phosphate buffer pH 6.8. FIG. 4 shows the dissolution profile of the Opadry® amb II film-coated ribociclib tablet in different pH media.

Example 8

Coated (with Opadry® Amb II Coating) 50 mg and 200 mg Ribociclib Tablets with Different Coating Premix Combination Table 5 below details the composition of film-coated 50 mg and 200 mg ribociclib tablets with different coating premix combination compared to Example 3. These tablets were made according to Steps 1-9 of the process flow diagram (FIGS. 1A-1B). The coating material is Opadry® amb II, which is commercially available and is an advanced moisture barrier (AMB) coating, PVA based.

TABLE 5

Composition per dosage form unit

| | Composition per unit [mg/unit] | |
|---|---|---|
| Ingredient | 50 mg of Ribociclib | 200 mg of Ribociclib |
| Inner phase | | |
| Ribociclib (LEE011) succinate[1] | 63.600 | 254.40 |
| Microcrystalline cellulose/ Cellulose, microcrystalline | 16.860 | 67.44 |
| Hydroxypropylcellulose | 12.030 | 48.12 |
| Crospovidone | 7.300 | 29.20 |
| Colloidal silicon dioxide/Silica, colloidal anhydrous | 0.530 | 2.12 |
| Magnesium stearate[2] | 1.590 | 6.36 |
| Outer phase | | |
| Crospovidone | 3.210 | 12.84 |
| Colloidal silicon dioxide/Silica, colloidal anhydrous | 0.265 | 1.06 |
| Magnesium stearate[2] | 2.115 | 8.46 |
| Core tablet weight | 107.500 | 430.00 |
| Coating[3] | | |
| Coating premix, white[4] | 4.201 | 16.804 |
| Coating premix, red[4] | 0.037 | 0.146 |
| Coating premix, black[4] | 0.062 | 0.25 |
| Purified water[5] | Qs | Qs |
| Film coated tablet weight | 111.800 | 447.20 |

[1]The salt factor is 1.272. The drug substance quantity is increased if the content is ≤99.5% with a corresponding reduction in the microcrystalline cellulose content.
[2]Vegetable origin
[3]Excess coating is prepared to compensate for losses during the coating process
[4]The coating premix is a commercially available product
[5]Removed during processing Example 9

Coated (with Opadry® Amb II Coating) 100 mg, 150 mg and 300 mg Ribociclib Tablets with Different Coating Premix Combination Table 6 below details the composition of film-coated 100 mg, 150 mg and 300 mg ribociclib tablets with different coating premix combination compared to Example 4. These tablets are made according to Steps 1-9 of the process flow diagram (FIGS. 1A-1B). The coating material is Opadry® amb II, which is commercially available and is an advanced moisture barrier (AMB) coating, PVA based.

TABLE 6

Composition per dosage form unit

| | Composition per unit [mg/unit] | | |
|---|---|---|---|
| Ingredient | 100 mg of Ribociclib | 150 mg of Ribociclib | 300 mg of Ribociclib |
| Inner phase | | | |
| Ribociclib (LEE011) succinate[1] | 127.2 | 190.8 | 381.6 |
| Microcrystalline cellulose/ Cellulose, microcrystalline | 33.72 | 50.58 | 101.16 |
| Hydroxypropylcellulose | 24.06 | 36.09 | 72.18 |
| Crospovidone | 14.60 | 21.9 | 43.8 |
| Colloidal silicon dioxide/Silica, colloidal anhydrous | 1.06 | 1.59 | 3.18 |
| Magnesium stearate[2] | 3.18 | 4.77 | 9.54 |
| Outer phase | | | |
| Crospovidone | 6.420 | 9.63 | 19.26 |
| Colloidal silicon dioxide/Silica, colloidal anhydrous | 0.53 | 0.795 | 1.59 |
| Magnesium stearate[2] | 4.23 | 6.345 | 12.69 |
| Core tablet weight | 215.00 | 322.5 | 645.00 |
| Coating[3] | | | |
| Coating premix, white[4] | 8.402 | 12.603 | 25.206 |
| Coating premix, red[4] | 0.074 | 0.111 | 0.222 |
| Coating premix, black[4] | 0.124 | 0.186 | 0.372 |
| Purified water[5] | Qs | qs | qs |
| Film coated tablet weight | 223.6 | 335.4 | 670.8 |

[1]The salt factor is 1.272. The drug substance quantity is increased if the content is ≤99.5% with a corresponding reduction in the microcrystalline cellulose content.
[2]Vegetable origin
[3]Excess coating is prepared to compensate for losses during the coating process
[4]The coating premix is a commercially available product
[5]Removed during processing

We claim:

1. A coated pharmaceutical oral tablet comprising tablet core and a coating, wherein the tablet core comprises at least 40% of ribociclib succinate (w/w), the coating comprises 45.52% polyvinyl alcohol (PVA), 20% talc, 2% lecithin, and 0.48% xanthan gum, and lacks hydroxypropyl methylcellulose (HPMC), and the tablet releases at least 75% of the ribociclib or its salt after 45 minutes when tested with the rotating basket at 100 rpm with 900 ml of dissolution media pH 2 or pH 4.5, at 37° C., according to United States Pharmacopeia (USP)<711>.

2. The tablet of claim 1 wherein the % of ribociclib succinate (w/w) is at least 50% of the tablet core.

3. The tablet of claim 2 wherein the % of ribociclib succinate (w/w) is at least 55% of the tablet core.

4. The tablet of claim 3, wherein the % of ribociclib succinate (w/w) is at about 55% to 65% of the tablet core.

5. The tablet of claim 1 wherein the % of ribociclib (w/w) is at about 60% of the tablet core.

6. The coated tablet according to claim 1, wherein the coating comprises 32% iron oxide.

7. A coated tablet comprising a tablet core and a coating, wherein the tablet core comprises:
   (a) an inner phase comprising:
      (i) ribociclib succinate;
      (ii) microcrystalline cellulose;
      (iii) hydroxypropylcellulose;
      (iv) crospovidone;
      (v) colloidal silicon dioxide; and
      (vi) magnesium stearate; and
   (b) an outer phase comprising:
      (i) crospovidone;
      (ii) colloidal silicon dioxide;
      (iii) magnesium stearate; and
   wherein the ribociclib succinate is present in an amount of at least 40% by weight of the tablet core and wherein the coating comprises 45.52% polyvinyl alcohol (PVA), 20% talc, 2% lecithin, and 0.48% xanthan gum, and lacks hydroxypropyl methylcellulose (HPMC).

8. The coated tablet according to claim 7, wherein
   (a) the inner phase comprises:
      (i) 63.600 mg ribociclib succinate;
      (ii) 16.860 mg microcrystalline cellulose;
      (iii) 12.030 mg hydroxypropylcellulose;
      (iv) 7.300 mg crospovidone;
      (v) 0.530 mg colloidal silicon dioxide; and
      (vi) 1.590 mg magnesium stearate; and
   (b) the outer phase comprises:
      (i) 3.210 mg crospovidone;
      (ii) 0.265 mg colloidal silicon dioxide; and
      (iii) 2.115 mg magnesium stearate.

9. The coated tablet according to claim 7, wherein
   (a) the inner phase comprises:
      (i) 254.40 mg ribociclib succinate;
      (ii) 67.44 mg microcrystalline cellulose;
      (iii) 48.12 mg hydroxypropylcellulose;
      (iv) 29.20 mg crospovidone;
      (v) 2.12 mg colloidal silicon dioxide; and
      (vi) 6.36 mg magnesium stearate; and
   (b) the outer phase comprises:
      (i) 12.84 mg crospovidone;
      (ii) 1.06 mg colloidal silicon dioxide; and
      (iii) 8.46 mg magnesium stearate.

10. The coated tablet according to claim 7, wherein
    (a) the inner phase comprises:
       (i) 127.2 mg ribociclib succinate;
       (ii) 33.72 mg microcrystalline cellulose;
       (iii) 24.06 mg hydroxypropylcellulose;
       (iv) 14.60 mg crospovidone;
       (v) 1.06 mg colloidal silicon dioxide; and
       (vi) 3.18 mg magnesium stearate; and
    (b) the outer phase comprises:
       (i) 6.420 mg crospovidone;
       (ii) 0.53 mg colloidal silicon dioxide; and
       (iii) 4.23 mg magnesium stearate.

11. The coated tablet according to claim 7, wherein
    (a) the inner phase comprises:
       (i) 190.8 mg ribociclib succinate;
       (ii) 50.58 mg microcrystalline cellulose;
       (iii) 36.09 mg hydroxypropylcellulose;
       (iv) 21.9 mg crospovidone;
       (v) 1.59 mg colloidal silicon dioxide; and
       (vi) 4.77 mg magnesium stearate; and
    (b) the outer phase comprises:
       (i) 9.63 mg crospovidone;
       (ii) 0.795 mg colloidal silicon dioxide; and
       (iii) 6.345 mg magnesium stearate.

12. The coated tablet according to claim 7, wherein
    (a) the inner phase comprises:
       (i) 381.6 mg ribociclib succinate;
       (ii) 101.16 mg microcrystalline cellulose;
       (iii) 72.18 mg hydroxypropylcellulose;
       (iv) 43.8 mg crospovidone;
    (v) 3.18 mg colloidal silicon dioxide; and
    (vi) 9.54 mg magnesium stearate; and
    (b) the outer phase comprises:
       (i) 19.26 mg crospovidone;
       (ii) 1.59 mg colloidal silicon dioxide; and
       (iii) 12.69 mg magnesium stearate.

13. The coated tablet according to claim 7, wherein the coating comprises 32% iron oxide.

14. The coated tablet according to claim 7, wherein the tablet releases at least 75% of the ribociclib or its salt after 45 minutes when tested with the rotating basket at 100 rpm with 900 ml of dissolution media pH 2 or pH 4.5, at 37° C., according to United States Pharmacopeia (USP)<711>.

* * * * *